United States Patent [19]
Schricker

[11] Patent Number: 5,596,513
[45] Date of Patent: Jan. 21, 1997

[54] METHOD AND APPARATUS FOR ESTIMATING INTERNAL BRAKE ENERGY

[75] Inventor: David R. Schricker, Dunlap, Ill.

[73] Assignee: Caterpillar Inc., Peoria, Ill.

[21] Appl. No.: 369,030

[22] Filed: Jan. 5, 1995

[51] Int. Cl.$^6$ .................................................. G01K 13/02
[52] U.S. Cl. .................... 364/557; 364/578; 364/426.01; 188/264 D; 188/71.6; 188/264 F
[58] Field of Search .................... 364/557, 559, 364/561, 578, 426.02, 426.03; 188/264 D, 264 F, 264 P, 264 R, 71.6, 269, 271, 272, 274, 276, 277, 280; 477/72, 76, 97, 98; 374/141, 110, 112, 45, 46–57

[56] References Cited

U.S. PATENT DOCUMENTS

| | | | |
|---|---|---|---|
| 4,161,116 | 7/1979 | Fegraus et al. | 73/117 |
| 4,828,089 | 5/1989 | Collins et al. | 192/70.12 |
| 5,136,508 | 8/1992 | Bannon et al. | 364/426.01 |
| 5,172,960 | 12/1992 | Chareire | 303/100 |
| 5,190,123 | 3/1993 | Hvolka | 188/71.6 |
| 5,400,018 | 3/1995 | Scholl et al. | 340/825.54 |

Primary Examiner—Ellis B. Ramirez
Assistant Examiner—Hien Vo
Attorney, Agent, or Firm—Jason J. Young

[57] ABSTRACT

A method and apparatus for estimating internal brake energy in a fluid cooled brake of the type used in large work machines from easily sensed machine operating parameters. The temperature of the coolant is sensed before and after it passes through the brake. The coolant flow rate through the brake is determined from one or more additional sensed parameters, for example engine speed. The sensed parameters are used in a thermodynamic model of the brake which generates estimates of internal brake temperature (TEIB) and the amount of power absorbed by the brake (BRKP). Signals representing TEIB and optionally BRKP are generated to provide indications of brake operation and/or health. The model is executed on a digital computer either on-board the vehicle or at a remote location.

27 Claims, 5 Drawing Sheets

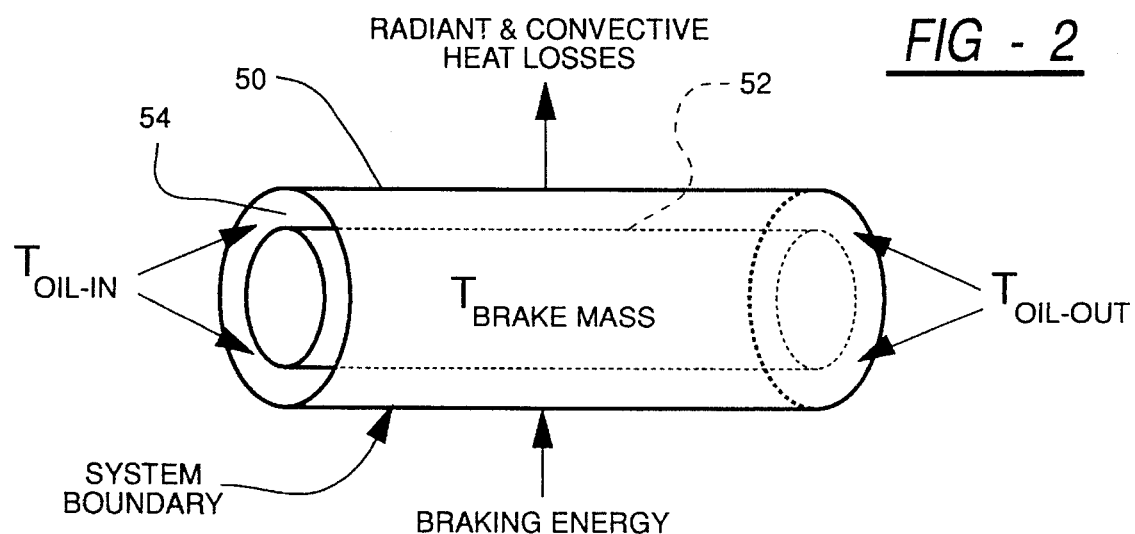
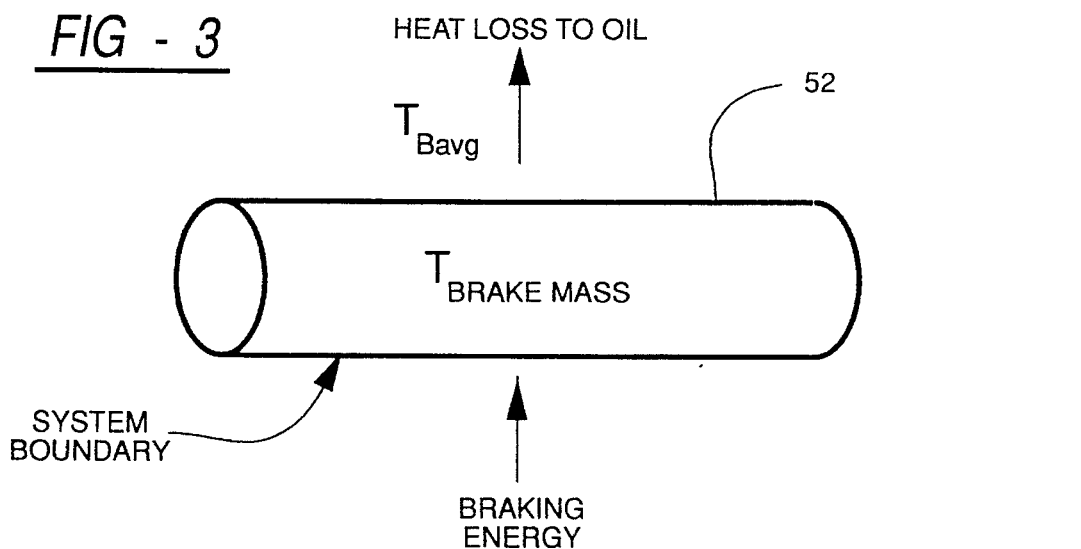
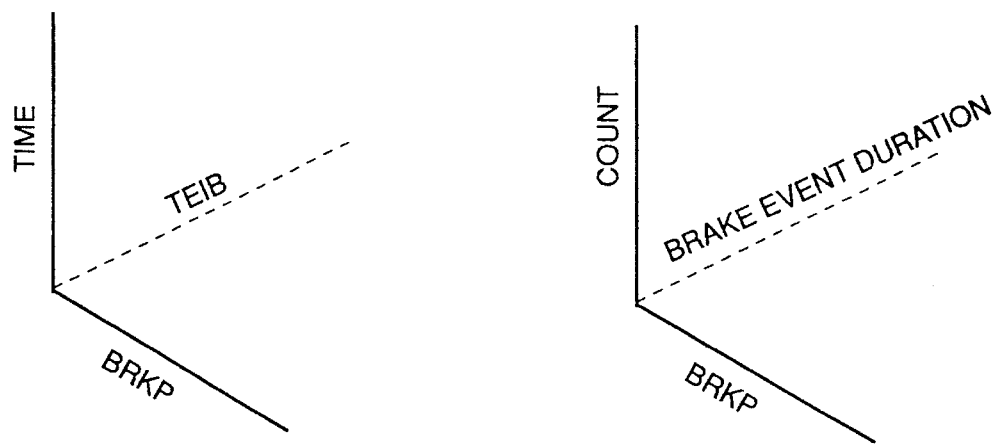

METHOD AND APPARATUS FOR ESTIMATING INTERNAL BRAKE ENERGY

TECHNICAL FIELD

This invention is in the field of fluid cooled braking systems for large work machines, such as on- and off-highway trucks, wheel loaders, track type tractors, graders and the like. More particularly, the invention is a method and apparatus for estimating internal brake energy from externally sensed parameters, which can be useful for evaluating brake operation and predicting brake life.

BACKGROUND OF THE INVENTION

Large work machines such as on- and off-highway trucks, wheel loaders, graders and track type tractors often employ braking systems in which a recirculating coolant fluid, often oil, is used to absorb and dissipate the heat produced in the brakes during braking action. Oil cooling is common on such vehicles due to their high operating weights and the consequent large amounts of kinetic energy transferred to the brakes as heat during braking.

Fluid-cooled brake components are typically sealed within a housing or casing which contains the coolant around the components. The energy generated in a braking event by these internal components, and energy-related brake operating parameters which can give an indication of brake operation or health, can therefore be described as internal.

Internal brake energy parameters such as internal brake temperature and absorbed brake power (i.e., the kinetic energy absorption rate) can affect component life. Trends of high internal brake temperature may indicate mechanical problems, improper brake use or reduced cooling fluid flow due to leaks in the system or a faulty pump. High brake friction material temperatures also cause premature brake wear and failure. Accordingly, knowledge of internal brake temperature and absorbed power can provide valuable indications of brake operation and remaining brake life. However, it is not practical to directly sense these internal brake energy operating parameters in the internal environment of the brake.

SUMMARY DISCLOSURE OF THE INVENTION

In general, the invention in a first aspect comprises a method for determining internal brake energy parameters for a fluid cooled brake on a work machine from easily (externally) sensed machine operating parameters. A thermal model of the brake is provided; machine operating parameters related to brake operation are sensed and input to the model; an estimated internal brake temperature (TEIB) is determined from the model based on the sensed parameters; and signals of TEIB are generated to provide indications of brake operation and/or health. Estimated internal brake temperature is useful in itself as an indicator of brake operation and remaining life, but the inventive method can include the additional step of determining absorbed brake power (BRKP) from the estimated internal brake temperature (TEIB) and generating signals of BRKP.

In a further aspect the inventive method includes the steps of providing a thermal model of the brake comprising an outer cylinder of negligible mass with high thermal resistance, a solid cylindrical brake mass centered coaxially within the outer cylinder, and an annular flow passage between the outer cylinder and the brake mass through which cooling fluid such as oil flows; determining from sensed machine operating parameters the temperature of oil into the brake ($TB_{in}$), the temperature of oil out of the brake ($TB_{out}$), and oil flow rate through the brake (BOF); defining a first braking energy system boundary for the model comprising the outer cylinder, and a second braking energy system boundary for the model comprising the brake mass; determining the estimated internal brake temperature (TEIB) from the first and second system boundaries and the sensor-based parameters ($TB_{in}$), ($TB_{out}$), and (BOF); and generating signals of TEIB useful for indicating brake operation and/or health. In a further form the method includes the additional step of determining absorbed brake power (BRKP) from the estimated internal brake temperature (TEIB) and sensor-based parameters, and generating signals of BRKP.

The invention in apparatus form comprises a thermal model of the brake stored in a digital storage and processing facility; sensors on the machine for generating signals representing machine operating parameters related to brake operation; means for receiving the sensor signals and inputting them into the model; and means for executing the model with the sensed parameters to determine an estimated internal brake temperature (TEIB), and for generating signals of TEIB useful for indicating brake operation and/or health. In a further form the invention includes means for determining absorbed brake power (BRKP) from the estimated internal brake temperature (TEIB) and the sensed parameters, and for generating signals of BRKP.

In a further aspect the inventive apparatus includes a thermal model of the brake stored in a suitable digital storage and processing facility, the brake model comprising an outer cylinder of negligible mass with high thermal resistance, a solid cylindrical brake mass centered coaxially within the outer cylinder, and an annular flow passage between the outer cylinder and the brake mass through which cooling fluid such as oil flows. Sensors are provided on the machine to sense the temperature of oil into the brake ($TB_{in}$), the temperature of oil out of the brake ($TB_{out}$), and one or more additional parameters from which oil flow rate through the brake (BOF) can be determined. The brake model further includes a first braking energy system boundary for the model comprising the outer cylinder, and a second braking energy system boundary for the model comprising the brake mass. Means are provided for inputting the sensor-based parameters $TB_{in}$, $TB_{out}$, and BOF to the model, and for executing the model for the first and second system boundaries with the sensor-based parameters to determine the estimated internal brake temperature (TEIB) and generate signals of TEIB useful for providing indications of brake operation and/or health. In a further form the means for executing the model further include means for determining kinetic energy absorbed by the brake (BRKP) from the estimated internal brake temperature (TEIB) and sensor based parameters.

The invention also includes other features and advantages that will become apparent from a more detailed study of the drawings and specification.

BRIEF DESCRIPTION OF THE DRAWINGS

FIG. 2 is a schematic representation of a model of an oil-cooled brake for implementing the method of the present invention;

FIG. 3 is a portion of the model in FIG. 2 representing a different system boundary;

BEST MODE FOR CARRYING OUT THE INVENTION

Figure 1:
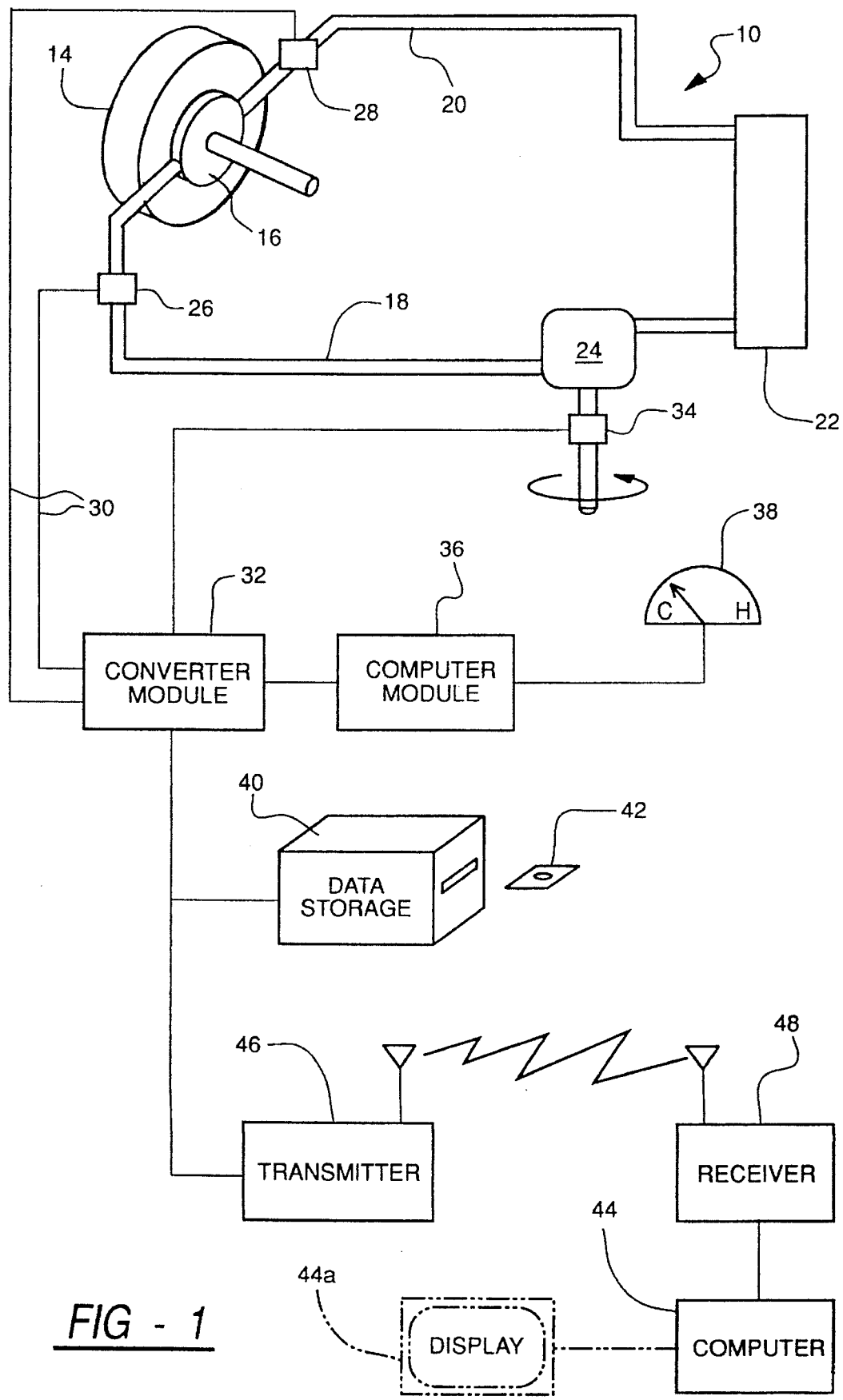
FIG. 1 is a schematic illustration of an oil-cooled brake and an exemplary system according to the present invention for determining internal brake energy.

Referring to FIG. 1, an oil cooled brake system 10 according to the present invention is schematically illustrated for a wheel on a work machine, for example an on- or off-highway truck. In brake system 10 a vehicle wheel 14 is provided with a brake 16, for example a drum brake or a disc-type brake, which is supplied with cooling oil by inlet line 18. The brake operating components are "internal," i.e. sealed within a housing or casing of brake 16 which contains the cooling oil around them. After passing through brake 16, the cooling oil flows through outlet line 20 to a heat exchanger 22 where it is cooled by another fluid such as air or water before being recirculated through the braking system by pump 24. In the illustrated embodiment pump 24 is powered by the main vehicle engine (not shown), and the oil flow rate through the brake 16 is a function of engine speed.

An oil inlet temperature sensor 26 is located in association with inlet line 18 in a position to sense the temperature of the cooling oil entering brake 16. Similarly, an oil outlet temperature sensor 28 is provided in association with outlet line 20 in a position to sense the temperature of cooling oil exiting brake 16. Sensors 26, 28 are known devices capable of producing electrical or other signals representing sensed temperature, for example thermo-couple devices producing an electrical signal proportional to the sensed temperature. The electrical signals travel via communication lines 30 to a converter module 32 where they are converted to a digital format compatible with microprocessor based devices.

The mass flow rate of cooling oil circulating through brake 16 varies with engine speed in the illustrated embodiment. A speed or rpm sensor 34 is located on pump 24 to generate a signal indicating pump speed. Alternately, engine speed can be sensed directly from the engine with known tachometer or other devices, and a corresponding signal delivered to convertor 32. The signal is supplied to converter module 32 for conversion to a digital format.

It will be understood that other sensed machine parameters can be used to generate signals from which oil flow rate can be determined, depending on the manner in which oil is circulated through the brake; engine speed is a preferred embodiment where oil flow rate is a function of engine speed.

Digital signals produced by converter module 32 are then supplied to a digital storage and processing facility such as a computer module 36, where a computer based model of the brake and an algorithm based on the model are stored and executed to calculate the internal brake temperature (TEIB), and optionally the amount of power absorbed by brake 16 (BRKP). One example of a computer that can perform the calculations required is a VIMS main module, available from Caterpillar, Inc. of Peoria, Ill. The calculated outputs are stored in memory of computer 36 and used by computer module 36 to generate signals representing TEIB and BRKP. These signals are relayed to one or more indicators or displays 38 carried onboard vehicle 12 for historical and/or real-time display to a vehicle operator or maintenance staff. Indicator(s) or display(s) 38 can comprise known apparatus such as lights, gauges, audio warnings, computer displays of graphical information and the like.

In a further embodiment of the invention, the digital signals generated by converter module 32 are relayed to a vehicle-mounted data storage module 40 where they are stored in resident memory and/or recorded on a physical data storage medium such as a floppy diskette or PC datacard 42. The recorded information in data storage module 40 is downloaded on a periodic basis, at the end of each day for example, to an offboard computer 44 at a remote location. Computer 44 stores and runs the brake model and processing necessary to calculate internal brake temperature and brake power based on the sensed parameter data from system 10, and generates signals representing temperature and power. The calculated outputs can be stored and the signals can be used to generate a display on an associated computer display 44a for review by maintenance personnel, or for diagnostic decision-making based on trend analysis.

In yet a further embodiment of the invention, the signals generated by converter module 32 are relayed to an onboard transmitter 46 for radio frequency transmission to an offboard receiver 48. Receiver 48 feeds the incoming signals to computer 44 for processing as described above.

While the system illustrated above is described for use with an oil-cooled brake, it is compatible with fluid cooled systems using coolants other than oil. The system is also not limited to use with wheel brakes, but can be used with brakes for track-type and other machines.

Referring to FIG. 2, the brake system is modeled as follows: an outer cylinder 50 of negligible mass and high thermal resistance surrounding a brake mass 52 which is considered to be a solid cylindrical core centered coaxially in the outer cylinder; and an annular oil flow passage defined between the outer cylinder 50 and the brake mass 52. Brake mass 52 models the internal brake components that are directly heated by the conversion of kinetic energy into thermal energy by friction within the brake. The model assumes kinetic energy is absorbed from some mechanism by the brake mass; for example, in a disc brake system brake mass 52 models a disc absorbing energy from caliper components. The annular opening between outer cylinder 50 and brake mass 52 models the passage for cooling oil through the brake, with thermal energy developed in brake mass 52 being transferred to the oil as it flows through the brake. The brake model can be used to model different known types of brake, and is not limited to disc-type brakes.

The method of the present invention uses a minimum number of easily sensed external parameters (e.g., $TB_{in}$, $TB_{out}$, engine speed) and the brake model to determine internal brake temperature and absorbed brake power based on those minimal sensor inputs. The following discussion of the model and its execution refers to the sensor inputs and a number of constant and calculated values, defined in the table below for easy reference:

|  | Type of Value |
|---|---|
| Input Values | |
| ESPD = Engine speed (rpm) | sensor |
| TBin = Brake oil in temperature (C) | sensor |
| TBout = Brake oil out temperature (C) | sensor |
| Kbr = Heat transfer coefficient of | constant |

-continued

| | Type of Value |
|---|---|
| brake mass (kW/C) | |
| MBR = Mass of working brake (kg) | constant |
| Kof = Flow constant for brake oil pump (liter/s-rpm) | constant |
| CPoil = Specific heat of oil (kJ/C-kg) | constant |
| CPbrk = Specific heat of brake mass (kJ/C-kg) | constant |
| OD = Oil density (kg/liter) | constant |
| TBavg = Average brake oil temperature (C) | calc |
| BOF = Brake oil flow (liter/s) | calc |
| RHL = Radiant heat loss (kW) | calc |
| CHL = Convective heat loss (kW) | calc |
| dT/dt = Time rate of change of brake mass temperature (C/s) | calc |
| Outputs | |
| TEIB = Estimated internal brake temperature (C) | output |
| BRKP = Power absorbed by brakes (kW) | output |
| Assumptions | |
| -RHL << BRKP, CHL << BRKP | |
| -RHL ≈ 0, CHL ≈ 0 | |
| -uniform brake temperature distribution | |

Definition of Relationships

For the case of a cooling oil pump driven directly from the vehicle engine $$BOF = K_{of} * ESPD$$

Also, $$TB_{avg} = (TB_{in} + TB_{out})/2$$

The brake model of FIG. 2 illustrates a first system boundary encompassing the modeled brake as a whole, defined by the outer cylinder 50. From the First Law of Thermodynamics ($\Sigma E = 0$), taking the system boundary in FIG. 2:

$$BRKP_{1t} = RHL + CHL + (TB_{out} - TB_{in}) * BOF * OD * CP_{oil} + dT/dt_{1t} * MBR * CP_{brk} \quad (1)$$

Referring to FIG. 3, a second system boundary is defined by the brake mass 52. Again applying the First Law of Thermodynamics, this time to the system boundary in FIG. 3:

$$BRKP_{1t} = dT/dt_{1t} * CP_{BRK} * MBR + (TEIB_{1t} - TB_{avg}) * K_{BK} \quad (2)$$

Combining equations (1) and (2) and solving for the internal brake temperature yields the relationship $$TEIB_{1t} = TB_{AVG} + [(TB_{OUT} - TB_{IN}) * BOF * OD * CP_{OIL}] \div K_{BR} \quad (3)$$

Performing numerical differentiation on equation (3) yields $$\frac{dT}{dt}\bigg|_{t-1/2} \approx \frac{(TEIB_t - TEIB_{t-1})}{\Delta t} \quad (4)$$

where $\Delta t$ is the sampling or execution rate of the model, for example one measurement per second. Extrapolating by one half $\Delta t$ yields:

$$\frac{dT}{dt}\bigg|_t \approx \frac{\left(3 * \frac{dT}{dt}\bigg|_{t-1/2}\right) - \frac{dT}{dt}\bigg|_{t-3/2}}{2} \quad (5)$$

All the terms are now defined for solving for $BRKP|_t$ from either equation (1) or equation (2). Accordingly, modeling the brake as shown in FIG. 2 and defining braking energy system boundaries as in FIGS. 2 and 3 provides a method for determining internal brake temperature and absorbed power based on the easily sensed inputs of $TB_{in}$, $TB_{out}$, and engine speed or other parameters which determine oil flow rate.

Figure 4:
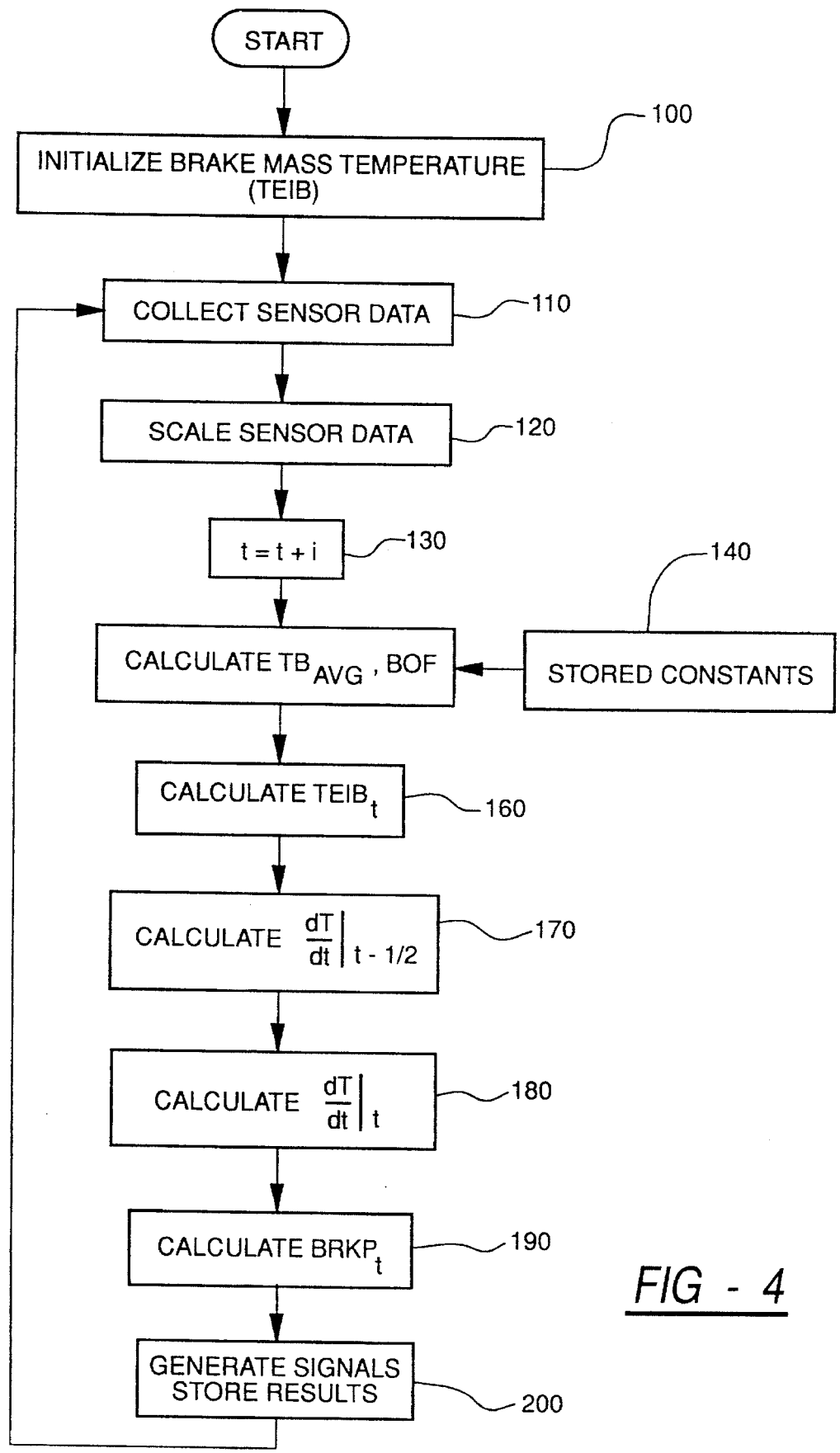
FIG. 4 is a flow chart showing an algorithm by which the present invention may be implemented.

FIG. 4 depicts the method of the invention in flow chart form as would be executed by a digital computer using the model and its algorithms described above. In Block 100, an initial brake mass temperature is utilized to begin the iterative process. This temperature may be a stored default value or a temperature reading from oil output temperature sensor 28. In Block 110, sensor data from oil temperature sensors 26, 28 and engine speed sensor 34 are collected at a predetermined sampling rate, and these sensor data are converted to digital values of the appropriate scale (degrees Celsius or rpm) in Block 120. The time value t is incremented in Block 130, and stored values of the brake system parameter constants are passed from Block 140 to Block 150 where $TB_{AVG}$ and BOF are calculated. In Blocks 160, 170, 180, and 190 the model is executed and equations (3), (4), (5) and (1) or (2) respectively are implemented, with the results stored in Block 200 and/or used to generate signals representing TEIB and BRKP. The system then returns to Block 110 to restart the iterative algorithm.

Figure 5:
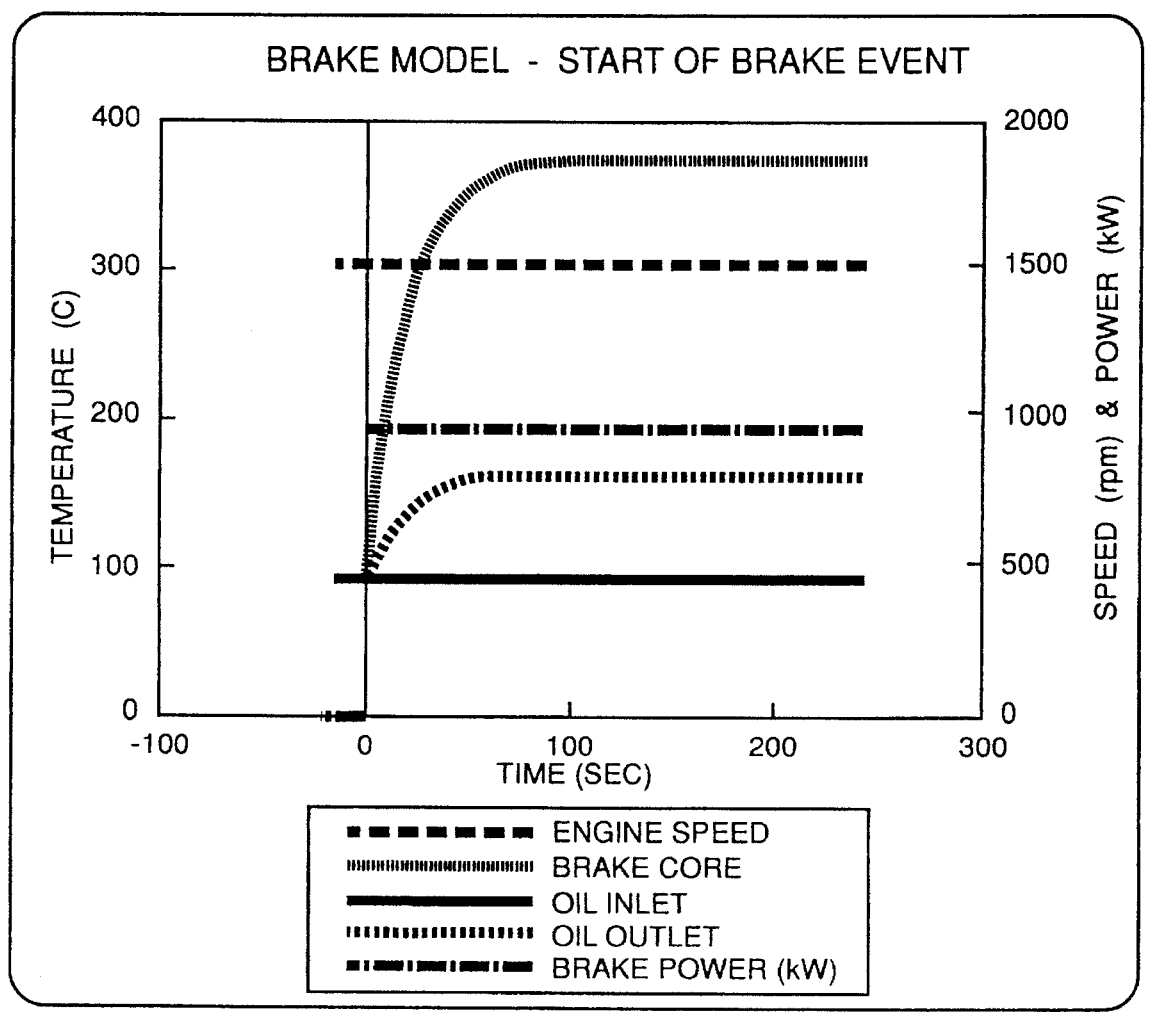
FIGS. 5 and 6 are graphic representations of brake energy output data generated by the system and method of the invention under different braking conditions; and, FIGS. 7 and 8 represent multi-dimensional histogram outlines useful for trending brake energy output data generated by the invention.
Figure 6:
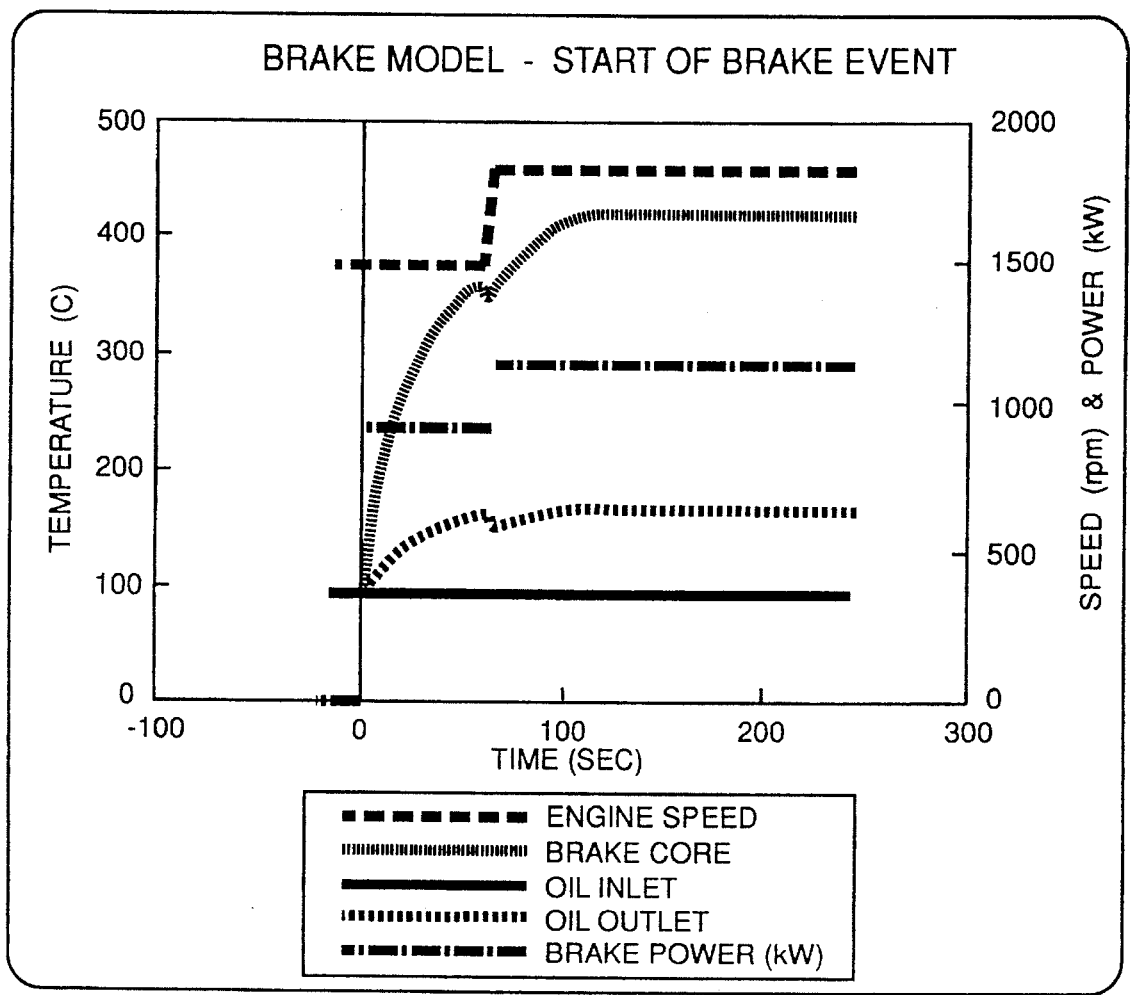

Referring now to FIGS. 5 and 6, the model and method of the present invention were executed on a computer in Lotus 123 for Windows V4.01. Constant values for the brake model were based on estimates for brake systems of the type employed by Caterpillar, Inc. on large on- and off-highway trucks in the 200 ton range. Other constants used in the simulation were estimated for reasonable machine operating values during braking conditions ($TB_{in}$, $TB_{out}$, engine speed) and various time and transient effect factors. The results were used to generate computer displays 44a, with FIG. 5 representing a plot of results of a braking system delivering 945 kW of braking power at 1500 rpm. The plot at FIG. 6 is similar to FIG. 5, except that at 60 seconds after initiating braking, engine speed was shifted to 1800 rpm and brake requirements were increased to 1130 kw. The results of brake core temperature (TEIB) and braking power (BRKP) at time t are clearly illustrated in the plotted data, with the results at the last measured point listed in the following tables on the display:

| TABLE FOR FIG. 5 | |
|---|---|
| Model Constants | |
| Kbr 3.85 (kW/C) | Heat Transfer Coefficient of Brake Mass |
| Kof 0.015 (lit/s-rpm) | Flow Constant For Oil Pump |
| CPoil 0.75 (kJ/C-kg) | Specific Heat of Oil |
| CPbrk 0.5 (kJ/C-kg) | Specific Heat of Brake Mass |
| OD 0.8 (kg/liter) | Oil Density |
| MBR 130 (kg) | Mass of Working Brake |
| Simulation Constants | |
| TinB 90 C | Steady State Input Temp |
| TinT 0.03 | Time Constant |
| TStep 1 (sec) | Time Step of Model |
| ToutB 160 C | Steady State Output Temp |
| ToutT 0.05 | Time Constant |
| DTLIMIT 1E + 04 (C/s) | Limit Of dT/dt - Clip Transient Effects |
| SPEED1 1500 rpm | Speed From 0–60 Steps |
| SPEED2 1500 rpm | Speed From 61–Last Step |
| Results - Last Point | |
| Brake Core Temp 370 C | |
| Braking Power 945 kW | |

-continued

TABLE FOR FIG. 6

Model Constants

| | |
|---|---|
| Kbr 3.85 (kW/C) | Heat Transfer Coefficient of Brake Mass |
| Kof 0.015 (lit/s-rpm) | Flow Constant For Oil Pump |
| CPoil 0.75 (kJ/C-kg) | Specific Heat of Oil |
| CPbrk 0.5 (kJ/C-kg) | Specific Heat of Brake Mass |
| OD 0.8 (kg/liter) | Oil Density |
| MBR 130 (kg) | Mass of Working Brake |

Simulation Constants

| | |
|---|---|
| TinB 90 C | Steady State Input Temp |
| TinT 0.03 | Time Constant |
| TStep 1 (sec) | Time Step of Model |
| ToutB 160 C | Steady State Output Temp |
| ToutT 0.05 | Time Constant |
| DTLIMIT 1E + 04 (C/s) | Limit of dt/dt - Clip Transiet Effects |
| SPEED1 1500 rpm | Speed From 0–60 Steps |
| SPEED2 1800 rpm | Speed From 61–Last Step |

Results-Last Point

Brake Core Temp 420 C
Braking Power 1134 kW

It will be apparent to those skilled in the art that the displays 44a of FIGS. 5 and 6 are easily accomplished with the method and apparatus illustrated in FIGS. 1–4 using known computer and sensor equipment.

Industrial Applicability

The calculated internal brake temperature (TEIB) can be monitored by the vehicle operator in real time on indicator 38 as shown in FIG. 1, with temperatures above a certain value providing the operator with warning of abusive brake operations or a brake system malfunction. Observed trends of TEIB over a period of time can be used for brake component life prediction, for example indicating abuse of the brakes or reduced oil flow due to leaks or pump wear. The estimated brake power BRKP can be stored onboard or offboard the machine and used as an input to a brake life prediction model as well as to a dynamic vehicle model.

For further example, real time and/or historical displays of the sensed machine parameters, internal brake temperature and brake power as illustrated in FIGS. 5 and 6 can be generated and displayed on or off a machine for monitoring by a machine operator or a supervisor. Historical trends of TEIB and BRKP can be stored, for example in the memory of the computer in which the brake model is executed, and periodically displayed and reviewed to determine whether the brakes are operating, or being operated, properly over the trended period. Trends of TEIB and BRKP may also indicate remaining brake life; for example a long trend of high TEIB and/or BRKP could be compared to previously determined brake life predictions for an estimate of remaining brake life.

One possible method of trending TEIB and BRKP is with multi-dimensional histogram trends of the type shown in FIGS. 7 and 8. The histograms shown in FIGS. 7 and 8 are initialized for a machine when its brake system is overhauled. Over a trend period determined, for example, by time or counts based on braking events, TEIB, BRKP, and the duration of each brake event can be continuously monitored and calculated, and signals generated to update the histograms using known methods such as histogram cell accumulation. The histogram data can be periodically broadcast to a base station computer which estimates consumed brake life or predicts remaining brake life from a mapping function of brake life consumed, determined from previous trend or histogram data generated in field testing. Supervisory personnel or diagnostic software at the base station can then schedule brake maintenance when the remaining brake life is determined to be less than a predetermined safety margin.

It should be understood that the above-described brake model can be executed by a computer comprising either a dedicated digital circuit or a general purpose microprocessor running appropriately designed software.

The foregoing description is of an illustrative embodiment only, and is not intended to limit the invention beyond the scope of the appended claims.

I claim:

1. A method for determining internal brake energy for a fluid cooled brake system on a work machine from easily sensed actual machine operating parameters, comprising the following steps:

providing a thermal model of the brake;

sensing actual machine operating parameters related to brake operation externally of the brake and inputting the sensed parameters to the model; and determining an estimated internal brake temperature (TEIB) from the model based on the sensed parameters, and generating signals of TEIB useful for indicating brake operation and/or health;

wherein the sensed parameters comprise the temperature of coolant into the brake ($TB_{in}$), the temperature of coolant out of the brake ($TB_{out}$), and one or more additional actual parameters from which the coolant flow rate through the brake (BOF) can be determined.

2. The method of claim 1, wherein coolant flow rate through the brake is a function of engine speed, and the additional sensed parameter is engine speed (ESPD).

3. The method of claim 1, further including the step of determining power absorbed by the brake (BRKP) from TEIB as a function of the rate of change of TEIB (dT/dt), and generating signals of BRKP useful for indicating brake operation and/or health.

4. The method of claim 1, wherein the thermal model of the brake comprises an outer cylinder of negligible mass with high thermal resistance, a solid cylindrical brake mass centered coaxially within the outer cylinder, and an annular flow passage between the outer cylinder and the brake mass through which the coolant flows.

5. The method of claim 4, wherein the step of determining (TEIB) from the brake model based on the sensed parameters includes the steps of defining a first system boundary for the brake model comprising the outer cylinder, defining a second system boundary for the brake model comprising the brake mass, and determining (TEIB) as a function of the first and second system boundary definitions.

6. The method of claim 1, wherein the step of generating signals of TEIB includes the step of generating a display of estimated internal brake temperature (TEIB) onboard the work machine.

7. The method of claim 1, wherein the step of generating signals of TEIB includes the step of generating a display of estimated internal brake temperature (TEIB) off the machine.

8. The method of claim 7, wherein the thermal model of the brake is stored in a digital processing facility off the machine, signals representing the sensed machine operating parameters are generated by sensors on the machine, and the signals are delivered to the thermal model off the machine to determine estimated internal brake temperature (TEIB).

9. A method for determining internal brake energy for a fluid cooled brake system on a work machine from easily sensed machine operating parameters, comprising the following steps:

provide a thermal model of the brake comprising an outer cylinder of negligible mass with high thermal resistance, a solid cylindrical brake mass centered coaxially within the outer cylinder, and an annular flow passage between the outer cylinder and the brake mass through which coolant flows;

determining from sensed machine operating parameters the temperature of coolant into the brake ($TB_{in}$), the temperature of coolant out of the brake ($TB_{out}$), and coolant flow rate through the brake (BOF);

defining a first braking energy system boundary for the model comprising the outer cylinder, and a second braking energy system boundary for the model comprising the brake mass; and, determining the estimated internal brake temperature (TEIB) from the first and second system boundaries and the sensor-based parameters ($TB_{in}$), ($TB_{out}$), and (BOF), and generating signals of TEIB useful for indicating brake operation and/or health.

10. The method of claim 9, further including the steps of determining the rate of change of TEIB (dT/dt), determining power absorbed by the brake (BRKP) from dT/dt, and generating signals of BRKP useful for indicating brake operation and/or health.

11. The method of claim 9, wherein coolant flow rate (BOF) is determined from sensed engine speed.

12. A method as defined in claim 9, wherein values of TEIB and BRKP are stored to provide historical indications of brake operation.

13. A method for estimating the internal brake energy in a fluid cooled brake on a work machine from easily sensed machine operating parameters, comprising the following steps:

sensing the machine operating parameters of temperature of coolant into the brake ($TB_{in}$), the temperature of coolant out of the brake ($TB_{out}$), and at least one additional machine operating parameter from which coolant flow through the brake (BOF) can be determined;

calculating the average brake coolant temperature ($TB_{avg}$);

calculating the brake coolant flow (BOF);

providing a thermal model of the brake comprising an outer cylinder of negligible mass with high thermal resistance, a solid cylindrical core centered coaxially within the outer cylinder, and an annular flow passage between the core and the outer cylinder;

determining the estimated internal brake temperature (TEIB) as a function of the brake model and the sensed parameters, and generating signals of TEIB useful for indicating brake operation and/or health.

14. The method of claim 13, further including the step of determining the power absorbed by the brake (BRKP) from TEIB and at least some of the sensed parameters.

15. The method of claim 14, further including the steps of determining the rate of change of TEIB (dT/dt), determining BRKP as a function of dT/dt, and generating signals of BRKP useful for indicating brake operation and/or health.

16. An apparatus for determining internal brake energy for a fluid cooled brake system on a work machine from easily sensed actual machine operating parameters, comprising:

a thermal model of the brake stored in a digital storage and processing facility;

sensors on the machine for generating signals representing actual machine operating parameters related to brake operation, the sensors being located externally of the brake;

means for receiving the sensor signals and inputting them to the brake model; and means for executing the model with the sensed parameters to determine an estimated internal brake temperature (TEIB), and means for generating signals of TEIB useful for indicating brake operation and/or health;

wherein the sensors include a brake inlet temperature sensor, a brake outlet temperature sensor, and one or more additional sensors from which the coolant flow rate through the brake can be determined.

17. The apparatus of claim 16, wherein the coolant flow rate through the brake is a function of engine speed, and the additional sensor is an engine speed sensor.

18. The apparatus of claim 16, further including means for determining power absorbed by the brake (BRKP) from the estimated internal brake temperature (TEIB), and means for generating signals of BRKP useful for indicating brake operation and/or health.

19. The apparatus of claim 16, wherein the thermal model of the brake comprises an outer cylinder of negligible mass with high thermal resistance, a solid cylindrical brake mass centered coaxially within the outer cylinder, and an annular passage between the outer cylinder and the brake mass through which the coolant flows.

20. The apparatus of claim 19, wherein the model includes a first braking energy system boundary comprising the outer cylinder, and a second braking energy system boundary comprising the brake mass.

21. The apparatus of claim 16, wherein the means for generating signals of TEIB includes means for displaying the estimated internal brake temperature (TEIB) onboard the machine.

22. The apparatus of claim 16, wherein the means for generating signals of TEIB includes means for displaying the estimated internal brake temperature (TEIB) offboard the machine.

23. The apparatus of claim 22, wherein the thermal model of the brake is stored in a digital processing facility off the machine, and the signals generated by the sensors on the machine are delivered offboard to the brake model to determine estimated internal brake temperature (TEIB).

24. An apparatus for determining internal brake energy for a fluid cooled brake system on a work machine from easily sensed machine operating parameters, comprising:

a thermal model of the brake stored in a digital storage and processing facility, the brake model comprising an outer cylinder of negligible mass with high thermal resistance, a solid cylindrical brake mass centered coaxially within the outer cylinder, an annular flow passage between the outer cylinder and the brake mass through which coolant flows, a first braking energy system boundary comprising the outer cylinder, and a second braking energy system boundary comprising the brake mass;

sensors on the machine for sensing the temperature of oil into the brake ($TB_{in}$), the temperature of oil out of the brake ($TB_{out}$), and coolant flow rate through the brake (BOF);

means for inputting the sensor-based signals to the model; and means for executing the model for the first and second system boundaries and the sensor-based signals to determine the estimated internal brake temperature (TEIB), and means for generating signals of TEIB useful for indicating brake operation and/or health.

25. The apparatus of claim 24, further including means for determining the rate of change of (TEIB) dT/dt, power absorbed by the brake (BRKP) from dT/dt and at least the sensor-based signals $TB_{in}$ and $TB_{out}$, and for generating signals of BRKP useful for indicating brake operations and/or health.

26. The apparatus of claim 24, wherein coolant flow rate (BOF) is a function of engine speed.

27. The apparatus of claim 24, further including means for storing values of TEIB and BRKP and for displaying historical trends of TEIB and BRKP.

* * * * *